United States Patent [19]
Tobia et al.

[11] Patent Number: 5,662,099
[45] Date of Patent: Sep. 2, 1997

[54] DETECTION OF BELLOWS COLLAPSED CONDITION IN MEDICAL VENTILATOR

[75] Inventors: Ronald L. Tobia, Sun Prairie; Kevin G. Tissot, Brooklyn; Carl H. Hendrickson; Steven K. Somerson, both of Madison, all of Wis.

[73] Assignee: Ohmeda Inc., Liberty Corner, N.J.

[21] Appl. No.: 624,070

[22] Filed: Mar. 29, 1996

[51] Int. Cl.$^6$ .......................... A62B 7/04; A61M 16/00; F16K 31/26; G08B 3/00
[52] U.S. Cl. ................ 128/205.15; 128/204.28; 128/202.22; 128/205.13
[58] Field of Search .............. 128/204.18, 204.21, 128/204.28, 205.13, 205.17, 205.23, 202.22; 417/63, 472

[56] References Cited

U.S. PATENT DOCUMENTS

| | | | |
|---|---|---|---|
| 2,578,265 | 12/1951 | Saalfrank | 417/63 |
| 2,880,719 | 4/1959 | Andreasen | 128/205.15 |
| 3,033,195 | 5/1962 | Gilroy et al. | 128/205.15 |
| 3,831,595 | 8/1974 | Valenta et al. | 128/205.15 |
| 5,237,310 | 8/1993 | Smith | 417/63 |
| 5,398,675 | 3/1995 | Henkin et al. | 128/205.15 |
| 5,490,499 | 2/1996 | Heinonen et al. | 128/205.15 |

*Primary Examiner*—Kimberly L. Asher
*Attorney, Agent, or Firm*—Roger M. Rathbun; Salvatore P. Pace

[57] ABSTRACT

An improved system for the determining the collapse of a bellows within a canister as part of a ventilator system for delivering breaths to a patient via a patient circuit. The system measures the pressure in the bellows canister external of the bellows and measures the pressure within the interior of the bellow. A processor compares the pressures and determines when the pressure within the canister exceeds a predetermined offset in excess of the pressure within the interior of the bellows to conclude that the bellows is in a collapsed condition. In the preferred embodiment, the processor also uses, as input data, the flow delivered by the ventilator to the bellows canister to determine that offset value. When a bellows empty condition is determined, various actions can be taken, among them to signal an alarm and also to change various functions of the ventilator to prevent further difficulties in the overall system. In addition, the recognition of a bellows collapsed condition and an alarm or remedial action provides a safety measure to the patient in the event the pressure sensor that measures the pressure in the patient breathing circuit is missing or fails to a zero level.

19 Claims, 2 Drawing Sheets

DETECTION OF BELLOWS COLLAPSED CONDITION IN MEDICAL VENTILATOR

BACKGROUND OF THE INVENTION

This invention relates to medical ventilators having a free standing bellows and, more particularly, to a system for determining a bellows collapsed condition.

In general, medical ventilator systems are used in the administration of anesthesia to a patient undergoing an operation and to maintain the patient under anesthesia until the cessation of the operation. Such systems include ventilators which provide a breath to the patient and which typically include a bellows in the system to separate the breathing circuit to which the patient is connected from the drive gas emanating from the ventilator. This is normally done in order to allow the partial reuse of the breathing circuit gases on successive breaths from the patient.

An advantage of such rebreathing in anesthesia systems is that the rebreathing of the gases allows the reuse of the expensive anesthetic agents that are added to such breathing gases. Thus, utilization of the anesthetic agent is reduced and the cost of using such agent is minimized.

Medical ventilator systems can incorporate several different types of bellows arrangements, including hanging, driven and standing type bellows. An example of a system incorporating a standing type bellows is shown and described in U.S. Pat. No. 5,315,989 of Tobia and which is assigned to the present assignee and the disclosure of which is hereby incorporated by reference, in that system, the standing bellows is driven pneumatically in a downward direction (gravity added) by the ventilator to expel the gas from inside the bellows to the patient circuit for breathing by the patient. The bellows is then allowed to rise back to its original position when the ventilator drive pressure is released as the patient exhales and additional fresh gas is admitted to the system, returning the bellows to its full up position.

By design, a standing bellows will collapse if its entire gas volume is exhausted. This is a relatively common occurrence that can be caused by uncompensated leaks or high ventilation demand. Under such conditions, it is possible for the bellows to deflate entirely and be pressed against the bottom of the bellows container by the drive pressure that continues to be administered to the interior of the bellows container.

When the bellows collapsed condition occurs, it is valuable to be able to alert the clinician of that condition so that remedial action can be taken. It is also desirable to prevent the ventilator from continuing to pin the bellows at the base of the bellows container with ever increasing drive pressure in a fruitless effort to deliver additional volume to the patient. Such conditions can seriously overpressure and stress the drive circuit of the ventilator. In addition, with the advent of closed loop control controlled ventilators, it is important to detect and react to this condition in order to prevent volume over-delivery on breaths subsequent to the causative condition being corrected and the bellows volume refilled.

SUMMARY OF THE INVENTION

The system of the present invention therefore corrects the aforedescribed problem by providing a system for detecting the bellows empty condition rapidly and reliably so that the remedial action can be taken and/or notice given to the clinician.

In particular, the present invention detects the bellows collapsed condition by monitoring the relative pressures on either side of the bellows, that is, one pressure transducer may be in the patient circuit and therefore provide a pressure reading indicative of the pressure in the interior of the bellows and another pressure transducer positioned so as to detect the pressure within the bellows container but exterior to the bellows. Alternatively, of course, a single differential pressure transducer can be employed to determine the difference in the pressure exterior of the bellows and interior of the bellows. By monitoring these pressures, it can be determined when the bellows is in the bellows collapsed condition and prompt audio and/or visual alarms can bring the condition to the attention of the clinician. Such action serves to improve patient safety as a collapsed bellows condition is often indicative that a patient ventilation problem exists.

Detection of the condition can further serve to automatically transition the ventilator into its exhalation cycle. This prevents the ventilator from continuing to drive the bellows downward with ever increasing drive pressures in a fruitless attempt to deliver volume to the patient. If the bellows collapsed condition is sensed during the exhalation cycle and PEEP is engaged, that PEEP can be disengaged for the remainder of the cycle.

As a further safety feature, if the pressure sensor in the patient circuit is missing or falls to a zero value, the present system will cycle to the exhalation phase and disable the established PEEP pressure.

For systems employing closed loop volume control, a detection of the bellows empty condition can be used to prevent feedback of indicated delivered tidal volume information. This will prevent the ventilator from increasing its drive gas output in a vain effort to achieve the set tidal volume amount either on the current breath or on subsequent breaths.

Other objects, features and advantages of the present invention will be more readily apparent from the detailed description of the preferred embodiment set forth below, taken in conjunction with the accompanying drawings.

DESCRIPTION OF THE PREFERRED EMBODIMENT

Figure 1:
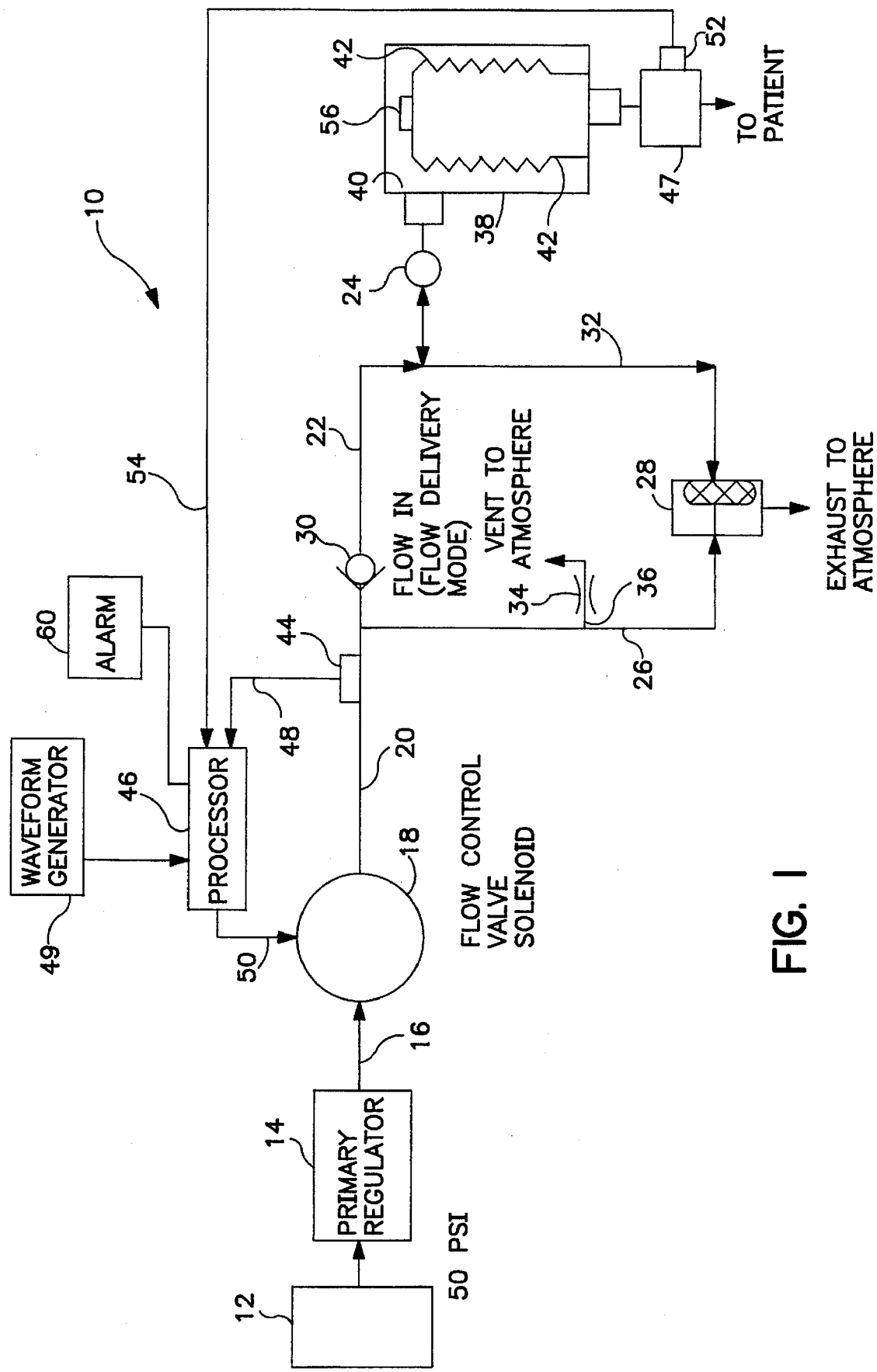
FIG. 1 is a schematic view of a ventilator apparatus suitable for carrying out the present invention.

Referring now to FIG. 1, there is shown a schematic view of a ventilator apparatus suitable for carrying out the present invention. The mechanical aspects of the ventilator apparatus are similar to those disclosed in U.S. Pat. No. 5,315,989 of Tobia and the disclosure of which is incorporated herein by reference, however, there are some differences in the systems and such differences will become apparent from the following description.

Ventilator 10 comprises a gas source 12 which typically provides gas at about 50 psi through a primary regulator 14 to source conduit 16 and which thus supplies flow control valve 18 with gas at approximately 26 psi. Flow control valve 18 is preferably a proportional solenoid valve and which controls the magnitude of gas flow into conduit 20. Conduit 22 communicates with conduit 20 and provides an inspiratory flow branch to ventilator connection 24. An expiratory flow branch is provided by conduit 32 which functions to convey gas from ventilator connection 24 to exhaust valve 28. Check valve 30 is located in conduit 22 to prevent flow from conduits 22 and 32 into conduit 20 during expiration of gas from ventilator connection 24.

Expiratory valve 28 controls the pressure and flow through conduit 32. Expiratory valve 28 is preferably a diaphragm or balloon type of valve which is capable of controlling the pressure in conduit 32 according to a reference pressure. Reference control pressure is provided to expiratory valve 28 via the pressure control conduit 26. A flow restrictor 34 is provided on vent conduit 36 to provide a bleed for the pressure control conduit 26. When gas pressure in expiratory conduit 32 exceeds the reference pressure in conduit 26, gas is exhausted from expiratory conduit 32 through expiratory valve 28 to the atmosphere. Thus, the pressure in expiratory conduit 32 is controlled by the reference pressure in pressure control conduit 26 which, in turn, is controlled by the flow control valve 18.

Ventilator connection 24 is made to a bellows assembly 38 and conduit 22 communicates with the bellows outer chamber 40 to actuate bellows 42. The patients breathing circuit 47 is in communication with the interior of the bellows 42 and thus is isolated from the gas in the ventilator 10.

Pressure sensor 44 communicates with the interior of conduit 20 and provides a signal indicative of the pressure within circuit 20 to processor 46 via a signal line 48. The pressure in conduit 20 will be referred to as the manifold pressure or $P_{MAN}$ and, as can be seen, is indicative of the pressure within the bellows outer chamber 40 exterior of the bellows 42. Processor 46 includes a microprocessor connected via an electronic bus to read only memory (ROM) and random access memory (RAM) in a known digital computer configuration.

Waveform generator 49 provides a desired waveform to processor 46. Flow control valve 18 is controlled by the processor 46 via a control signal line 50 to track the desired pressure waveform established by the user. Proximal airway pressure sensor 52, which is preferably located in the Y-piece of the patient circuit 47, also provides signals to processor 46 via the signal line 54. Accordingly, as can be seen, the proximal airway pressure sensor 52 determines a pressure that is indicative of the pressure within the bellows 42.

Conduits 20, 22 and 32 thus define a ventilator circuit which communicates with the ventilator connection 24. During most of the inspiratory phase of a patient breath, the ventilator 10 operates in the flow delivery mode whereby flow is delivered from gas source 12 through the flow control valve 18 to conduits 20 and 22 and finally to the ventilator connection 24. During most of the expiratory phase of the patient breath, check valve 30 prevents flow from conduit 22 to conduit 20 and gas flows via conduit 32 to expiratory valve 28 where it is exhausted to the atmosphere. The ventilator thus operates in a flow exhaust mode.

As may now be seen, there are pressure sensors that can detect pressures indicative of the pressure on both sides of the bellows 42, that is, the pressure sensor 44 can detect the pressure within the bellows assembly 38 external to the bellows 42 while the proximal airway pressure sensor 52 can measure the pressure indicative of the internal volume of the bellows 42 via the patient breathing circuit 47. in each case, the pressure detected may be merely indicative of those pressures and the exact pressures are not necessary in carrying out the present invention, it being only necessary that the relative pressures be measured.

As an alternative to the use of separate pressure sensors to detect the pressure internal of the bellows and the pressure external of the bellows within the bellows assembly 38, a differential pressure sensor 56 can, of course, be positioned in the system so as to determine the difference between those two pressures and could conveniently be placed in the bellows itself to detect that differential pressure and send a signal indicative of the pressure difference. The differential pressure sensor could be a pressure differential switch that provides an indication or signal when the differential pressure exceeds the predetermined amount.

Figure 2:
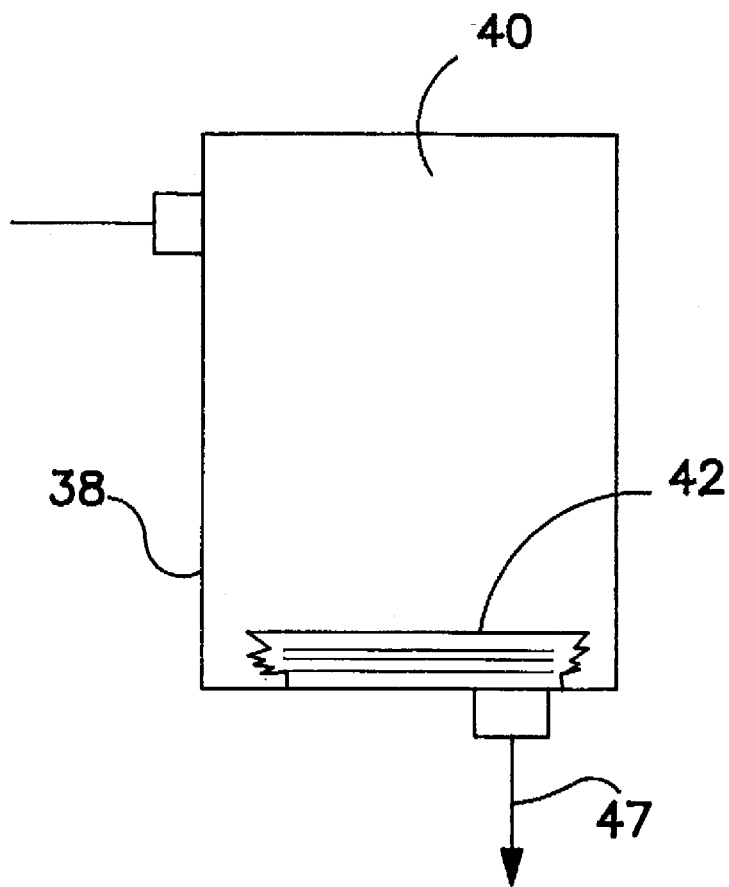
FIG. 2 is an enlarged schematic view of a bellows of the FIG. 1 configuration showing the bellows in the bellows empty condition.

Turning briefly to FIG. 2, there is shown a schematic view of a bellows 42 in the collapsed condition where it rests on the bottom of the assembly 38. As can be seen, at this point, the further addition of pressurized gas into the bellows assembly 38 will have no effect on the movement of the bellows 42 and the bellows assembly 38 will merely experience an increase in pressure. The pressure in the bellows assembly, and likewise the prior conduits and components of FIG. 1, can thus be overpressurized and potentially damaged.

The condition of FIG. 2 can thus be detected by a relationship between the differential pressure across the bellows 42. Returning briefly to FIG. 1, there are, as stated, pressure sensors that can measure the pressure on both sides of bellows 42. That is, the proximal airway pressure sensor 52 can provide an indication of the pressure in the patient airway or $P_{AIRWAY}$ which is, of course, indicative of the pressure inside of the bellows 42. Likewise, the pressure sensor 44 can provide an indication of the pressure within the bellows assembly 38 external of the bellows 42 ($P_{MAN}$).

Since both of those pressure readings are communicated to the processor 46, the processor 46 can readily monitor both of those pressures. In general, those pressures will track each other in the normal ventilator operation with some offset. Accordingly, the processor 46 can compare the values of such pressures and determine when the offset level exceeds a predetermined value. Such condition would indicate that the bellows is collapsed. Alternatively,the first derivative of the $P_{MAN}$ and $P_{AIRWAY}$ signals could be used where an increase in the first derivative of the $P_{MAN}$ signal without corresponding increase in the first derivative of the $P_{AIRWAY}$ signal would indicate a bellows empty condition.

In the preferred embodiment, however, the $P_{MAN}$ and $P_{AIRWAY}$ signals are used without differentiation. Referring again to FIG. 1, there exists a known offset function between $P_{MAN}$ and $P_{AIRWAY}$ dependent on the output flow from the flow control valve 18. The flow from the flow control valve 18 is, of course, the setting of that valve and is a value that is available to the processor 46. Accordingly as a preferred embodiment, the following formula can be used to determine the offset limit indicative of the bellows empty condition:

$$P_{MAN}(cm.H_2O) > 10 cm.H_2O + 0.125 \times \text{Ventilator flow rate} + P_{AIRWAY}(cm. H_2O),$$

where 10 cm.$H_2O$+0.125 cm.$H_2O$ min./liter×ventilator flow rate(liters/min.) is the offset limit.

When $P_{MAN}$ exceeds $P_{AIRWAY}$ plus the calculated offset limit, a collapsed or empty bellows condition is indicated. Based on the information, processor 46 proceeds to activate audio and/or visual alarm 60 so that the user can recognize the existence of the problem. Also in the preferred embodiment, alarm filters are employed during specific portions of the breathing cycle such as the beginning of inspiration in order to prevent false positives.

As previously indicated, the difference between $P_{MAN}$ and $P_{AIRWAY}$ could be detected by a differential pressure transducer or simply a differential pressure switch that provides an indication or signal when the difference in those pressures exceed the predetermined offset value.

Along with the alarm, or independently therefrom, the recognition of the empty bellows condition can be used to immediately change the ventilator 10 to its exhalation cycle. This will prevent the ventilator from increasing drive pressure in a vain effort to provide the set volume to the patient. If there is a positive PEEP pressure established at the time, the recognition of the bellows empty condition can generate a signal to discontinue that PEEP pressure until the termination of the normal exhalation cycle.

As a still further action, the signal representative of the bellows empty condition can be used to discontinue the collection of data on the volume delivered. This is important when utilizing ventilators employing closed loop volume control, for in such applications, the bellows empty condition constitutes a saturated control output. In order to prevent improper build-up of integrated control signal, closed loop feedback must be discontinued when a bellows empty condition exists.

While the present invention has been set forth in terms of a specific embodiment, it will be understood that the ventilator and bellows system herein disclosed may be altered or modified by those skilled in the art to other configurations. Accordingly, the invention is to be broadly construed and limited only by the scope and spirit of the claims appended hereto.

We claim:

1. A ventilator system for providing a breath to a patient connected to a patient circuit and for receiving exhaled gases from the patient, said system comprising a ventilator, a bellows canister containing a collapsible bellows, a drive conduit fluidly connecting said ventilator to said bellows canister, said ventilator supplying a quantity of gas through said drive conduit to compress said bellows to deliver gas from the interior of said bellows to the patient circuit, a first pressure sensor to detect the pressure indicative of the pressure within the interior of said bellows and to provide a first signal representing that pressure, a second pressure sensor to detect the pressure indicative of the pressure within said bellows canister exterior of said bellows and to provide a second signal representing that pressure, processor means responsive to said first and said second signals to determine that said bellows is in a fully collapsed condition.

2. A ventilator system as defined in claim 1 wherein said processor is a microprocessor controlling said ventilator.

3. A ventilator system as defined in claim 2 wherein said microprocessor determines said bellows is in a fully collapsed condition by comparing said first and second signals and determines the bellows collapsed condition when first signal rises at a rate exceeding the rate of rise of said second signal by a predetermined rate.

4. A ventilator system as defined in claim 2 wherein said microprocessor determines said bellows is in a fully collapsed condition by comparing said first and second signals and determines the bellows collapsed condition when said first signal exceeds said second signal by a predetermined offset.

5. A ventilator system as defined in claim 4 wherein said predetermined offset is a function of a ventilator parameter and said microprocessor calculates said predetermined offset.

6. A ventilator system as defined claim 5 wherein said predetermined offset is calculated by said microprocessor by using the flow rate of gas from said ventilator.

7. A ventilator system as defined claim 6 wherein said predetermined offset is calculated by said microprocessor in accordance with the following:

Offset=10cm.$H_2O$+0.125×Ventilator flow rate.

8. A ventilator system as defined in claim 2 wherein said system further comprises an alarm that is activated by said microprocessor when said microprocessor determines said bellows is fully collapsed.

9. A ventilator system as defined in claim 2 wherein said alarm system includes alarm filters employed during certain portions of the breathing cycle to prevent false positives.

10. A ventilator system as defined in claim 2 wherein said microprocessor determines a bellows collapsed condition by calculating the first derivative of said first signal and the first derivative of said second signal and determines the bellows collapsed condition when said first derivative of said first signal exceeds the first derivative of said second signal by a predetermined amount.

11. A ventilator system as defined in claim 1 wherein said first pressure sensor is located in said drive conduit supplying gas to said bellows canister and said second pressure sensor is located in the patient circuit.

12. A ventilator system for providing a breath to a patient connected to a patient circuit during an inhalation cycle and for receiving exhaled gases from the patient during an exhalation cycle, said system comprising a ventilator, a bellows canister containing a collapsible bellows, a drive conduit fluidly connecting said ventilator to said bellows canister, said ventilator supplying a quantity of gas through said drive conduit to compress said bellows to deliver gas from the interior of said bellows to the patient circuit, differential pressure sensor means to determine the difference in the pressure indicative of the pressure within the interior of said bellows and the pressure indicative of the pressure within said bellows canister exterior of said bellows, said differential pressure sensor adapted to determine a bellows collapsed condition when said differential pressure exceeds a predetermined offset value.

13. A ventilator system as defined in claim 12 wherein said system includes an alarm and said means to determine when said differential pressure exceeds a predetermined amount provides a signal to activate said alarm.

14. A ventilator system as defined in claim 12 wherein said means to determine when said differential pressure exceeds a predetermined amount provides a signal to switch said ventilator to said exhalation cycle.

15. A ventilator system as defined in claim 12 wherein said predetermined offset value is calculated based on the flow of gas from said ventilator during said inhalation cycle.

16. A method of determining when a bellows is fully collapsed in a medical ventilator system comprising the steps of:

providing a ventilator to administer a breath to a patient and to receive a breath from the patient, providing a bellows canister containing a collapsible bellows, collapsing the bellows by forcing a drive gas at a known pressure from the ventilator through a drive gas conduit into the bellows canister external of the bellows to compress the bellows to provide a breath to the patient from the interior of the bellows, sensing the pressure in the canister external of the bellows, sensing the pressure within the interior of the bellows, comparing the sensed pressures to determine the bellows empty condition.

17. A method as defined in claim 16 wherein said step of comparing said sensed pressures comprises calculating an offset between the sensed pressure external of the bellows and the pressure within the interior of the bellows and determining a collapsed bellows condition when the pressure external of the bellows exceeds the pressure within the interior of the bellows by the calculated offset.

18. A method as defined in claim 16 wherein the step of calculating the offset comprises calculating that offset by using the following equation:

$$\text{Offset} = 10 \text{cm.H}_2\text{O} + 0.125 \times \text{Ventilator flow rate.}$$

19. A method as defined in claim 17 wherein the step of comparing said sensed pressures comprises calculating the first derivative of the pressure external of the bellows and calculating the first derivative of the pressure within the interior of the bellows and determining a bellows collapsed condition where the first derivative of the pressure external of the bellows exceeds the first derivative of the pressure within the interior of the bellows by a predetermined amount.

* * * * *